United States Patent
Glazer et al.

(10) Patent No.: US 12,364,525 B2
(45) Date of Patent: Jul. 22, 2025

(54) BENDABLE ORTHOPEDIC FASTENERS

(71) Applicant: SG, LLC, Boston, MA (US)

(72) Inventors: Paul Glazer, Boston, MA (US); Michael J. Milella, Jr., Escondido, CA (US)

(73) Assignee: SG, LLC, Boston, MA (US)

( * ) Notice: Subject to any disclaimer, the term of this patent is extended or adjusted under 35 U.S.C. 154(b) by 306 days.

(21) Appl. No.: 18/126,201

(22) Filed: Mar. 24, 2023

(65) Prior Publication Data

US 2024/0315746 A1  Sep. 26, 2024

(51) Int. Cl.
*A61B 17/86* (2006.01)

(52) U.S. Cl.
CPC ........ *A61B 17/864* (2013.01); *A61B 17/8635* (2013.01)

(58) Field of Classification Search
CPC .. A61B 17/869; A61B 17/8685; A61B 17/864
See application file for complete search history.

(56) References Cited

U.S. PATENT DOCUMENTS

| | | | |
|---|---|---|---|
| 4,913,137 A | 4/1990 | Azer et al. | |
| 5,061,137 A * | 10/1991 | Gourd | F16B 21/088 411/908 |
| 6,447,518 B1 | 9/2002 | Krause et al. | |
| 6,656,184 B1 * | 12/2003 | White | A61B 17/8625 606/318 |
| 7,175,626 B2 * | 2/2007 | Neff | A61B 17/8875 606/86 A |
| 8,197,523 B2 * | 6/2012 | Bottlang | A61B 17/863 606/301 |
| 8,353,935 B2 | 1/2013 | Krause | |
| 8,597,337 B2 * | 12/2013 | Champagne | A61B 17/863 606/315 |
| 9,482,260 B1 | 11/2016 | Krause | |
| 9,808,867 B2 | 11/2017 | Krause et al. | |
| 10,154,863 B2 * | 12/2018 | Fallin | A61B 17/7291 |
| 10,485,595 B2 * | 11/2019 | Fallin | A61B 17/863 |
| 10,842,535 B2 | 11/2020 | Krause | |
| 2009/0062868 A1 * | 3/2009 | Casutt | A61B 17/7001 606/301 |

(Continued)

FOREIGN PATENT DOCUMENTS

EP  3967251 A1  3/2022

*Primary Examiner* — David W Bates
(74) *Attorney, Agent, or Firm* — Troutman Pepper Locke LLP; Joshua L. Jones; Gabrielle L. Gelozin

(57) ABSTRACT

In accordance with at least one aspect of this disclosure, a flexible fastener includes, a shaft having a proximal end and a distal end spaced apart along a longitudinal axis and a land surface winding helically around the shaft. An interior pocket extends in an axial direction inside the shaft, radially inward from the land surface. A flexure opening extends through the shaft in the radial direction from the land surface to an inward facing surface of the interior pocket. The flexure opening extends helically about the longitudinal axis to provide for flexure of the shaft, of the land surface, and of the external thread. A torque driver is seated in the interior pocket, the toque driver having a torque face configured to abut a torque face of the interior pocket to develop toque along the shaft when a driving torque is applied to the proximal end of the shaft.

20 Claims, 8 Drawing Sheets

(56) References Cited

U.S. PATENT DOCUMENTS

| | | | |
|---|---|---|---|
| 2009/0149890 A1* | 6/2009 | Martin | A61B 17/1728 606/301 |
| 2010/0292695 A1* | 11/2010 | May | A61B 17/1655 606/64 |
| 2011/0144703 A1* | 6/2011 | Krause | A61B 17/869 606/309 |
| 2014/0114312 A1* | 4/2014 | Krause | A61B 17/864 606/62 |
| 2014/0163624 A1* | 6/2014 | Siegal | A61B 17/7032 606/304 |
| 2015/0012048 A1* | 1/2015 | Huebner | A61B 17/8685 606/304 |
| 2015/0039033 A1* | 2/2015 | Biedermann | B22F 10/20 264/154 |
| 2017/0189085 A1 | 7/2017 | Krause | |
| 2018/0092681 A1* | 4/2018 | Lutz | A61B 17/8685 |
| 2020/0262038 A1 | 8/2020 | Krause et al. | |
| 2021/0121212 A1 | 4/2021 | Krause | |
| 2022/0240997 A1 | 8/2022 | Krause et al. | |
| 2023/0404636 A1* | 12/2023 | Whittaker | A61B 17/8685 |

\* cited by examiner

BENDABLE ORTHOPEDIC FASTENERS

BACKGROUND

1. Field

The present disclosure relates to fasteners, and more particularly to flexible fasteners such as for use in orthopedic applications.

2. Description of Related Art

A typical screw includes a shaft extending from a head. A helical thread winds around the shaft so that torque applied to the head rotates the threads to drive the screw into two or more substrates to join the substrates together. In some cases one or more of the substrates may be prepared with a female thread for engaging the male thread of the screw. Other screws are self-tapping and do not require pre-threaded bores in the substrates being joined.

There a variety of orthopedic application for screws, i.e. bone screws. Bone screws can be used to join to pieces of a bone together, e.g. such as in treatment of trauma. In other procedures, bone screws can be used to anchor an implant to bone, such as in an artificial hip replacement or a spinal implant.

Some bendable fasteners such as screws have allowed for a bone screw to flex as it is being driven so that the tip of the screw ultimately points a different direction from the driver driving the head. This can be beneficial, for example where minimally invasive surgical site access limits a surgeon's mobility with the driver. Example applications of a bendable screws and other fasteners for various implants are described in U.S. Pat. No. 9,597,199 to Glazer.

There has been a tradeoff in designing bendable screws using conventional methods. The more flexible the fastener, the more likely it is to break while being driven. The stronger the fastener is for transmitting torque and avoiding breakage while being driven, the less flexible it tends to be.

The conventional techniques have been considered satisfactory for their intended purpose. However, there is an ever present need for improved systems and methods for bendable fasteners such as for use in orthopedic applications. This disclosure provides a solution for this need.

SUMMARY

In accordance with at least one aspect of this disclosure, a flexible fastener includes, a shaft having a proximal end and a distal end spaced apart along a longitudinal axis and a land surface winding helically around the shaft. An interior pocket extends in an axial direction inside the shaft, radially inward from the land surface. A flexure opening extends through the shaft in the radial direction from the land surface to an inward facing surface of the interior pocket. The flexure opening extends helically about the longitudinal axis to provide for flexure of the shaft, of the land surface, and of the external thread. A torque driver is seated in the interior pocket, the toque driver having a torque face configured to abut a torque face of the interior pocket to develop toque along the shaft when a driving torque is applied to the proximal end of the shaft.

In embodiments, the torque driver can be free floating (e.g., not integral with or affixed to) within the interior pocket when the shaft is in a relaxed state where no torque is applied to the shaft. In embodiments, the torque driver can include a proximal portion and a distal portion with a narrowing neck connecting the distal portion to the proximal portion. In certain embodiments, the torque face of the torque driver can be a first torque face of the proximal portion of the torque driver and the proximal portion of the torque driver can include at least one additional torque face. In embodiments, the distal portion of the torque driver can include a plurality of torque faces.

In embodiments, the interior pocket can include a proximal portion housing the proximal portion of the torque driver. The interior pocket can also include a distal portion housing the distal portion of the torque driver. In embodiments, the interior pocket can define a narrowing neck connecting between the proximal and distal portions of the interior pocket through which the narrowing neck of the torque driver passes.

In embodiments, each of the torque faces of the distal portion of the torque driver can face a corresponding torque face of the distal portion of the interior pocket for abutment. In embodiments, each of the torque faces of the proximal portion of the torque driver can face a corresponding torque face of the proximal portion of the interior pocket for abutment.

In embodiments, a clearance gap can be defined between the toque driver and the interior pocket so the toque driver can move within the pocket as long as the shaft is in the relaxed state. The clearance gap, torque faces of the torque driver, and the torque faces of the interior pocket can be configured so the clearance gap is too small to allow the rotation of the torque driver about the longitudinal axis beyond a point where the torque faces of the interior pocket and of the torque driver come into abutment.

The distal and proximal portions of the torque driver can define a square axial cross-section with a diagonal too large to rotate within the interior pocket beyond abutment of the torque faces. In certain embodiments, abutment (e.g., as used here) may not necessarily require full planar contact or engagement. In embodiments, the proximal and distal portions of the torque driver can have a cul-de-sac cross-sectional shapes in a plane of the diagonal. In certain embodiments, the proximal and distal portions of the torque driver can be aligned along the same diagonal. In certain embodiments the proximal and distal portions of the torque driver can be clocked about the longitudinal axis relative to one another.

In certain embodiments, the narrowing neck of the torque driver can define a circular axial cross-section. In certain embodiments, the flexure opening can be too small to admit the torque driver therethrough so the torque driver is captured in the interior pocket. In embodiments, a proximal end of the flexure opening can be axially proximate a proximal end of the interior pocket with respect to the longitudinal axis. In embodiments, the flexure opening can wind around the interior pocket to a distal end of the flexure opening that is proximal to a distal end of the interior pocket. In certain embodiments, the flexure opening can bend beyond 360° around the interior pocket circumferentially relative to the longitudinal axis. In embodiments, the distal end of the flexure opening can define a distal stress-reducing cul-de-sac shape, and the proximal end of the flexure opening can define a proximal stress-reducing cul-de-sac shape.

In embodiments, the interior pocket can be a first interior pocket and the fastener can include a second interior pocket extending in an axial direction inside the shaft, radially inward from the land surface, and axially spaced apart from the first interior pocket by a solid internal wall of the shaft.

In certain embodiments, the flexure opening can overlap axially with the first interior pocket but not with the second interior pocket.

In certain embodiments, the interior pocket can be a first interior pocket in a plurality of interior pockets spaced apart axially along the longitudinal axis within the shaft. The torque driver can be a first torque driver in a plurality of torque drivers each seated in respective one of the plurality of interior pockets. In certain such embodiments, the flexure opening can be a first flexure opening in a plurality of flexure openings each opening into and overlapping axially with a respective one of the plurality of interior pockets. In certain embodiments, each of the flexure openings can have a proximal end and a distal end, where the proximal ends of the flexure openings can all terminate at a first circumferential position (e.g., a clock position) relative to the longitudinal axis and the distal ends of the flexure openings can all terminate at a second circumferential position relative to the longitudinal axis.

In embodiments, an external thread can wind helically round the shaft. The land surface can be wound helically around the shaft axially offset from the external thread so that the land surface alternates with the external thread in an axial direction along the shaft. The external thread can extend in a radial direction beyond the land surface, and the flexure opening can extend helically in parallel with the external thread. In certain embodiments, the fastener may not include any external thread (e.g., such as for use as an intramedullary nail).

In embodiments, a head can be included at the proximal end of the shaft configured to engage a driver for turning the fastener about the longitudinal axis. The distal end of the shaft can define a narrowing tip that tapers down along the longitudinal axis in a distal direction. In certain embodiments, the narrowing tip can include a self-tapping recess or a self-drilling feature.

In certain embodiments, the fastener can be additively manufactured and the torque drivers can be captured inside the interior pockets. In certain embodiments, the fastener can be of a metallic material, such as titanium or stainless steel. In certain embodiments, the fastener can be of a biocompatible material or a combination of one or more biocompatible materials. In certain embodiments, the fastener can be configured to bend up to and beyond 45° off of the longitudinal axis. In embodiments, the fastener can be used for orthopedic applications. In certain embodiments, the orthopedic applications can include, vertebral spacers, acetabular cups, glenoid fossa prostheses, scaphoid prostheses, cervical spine implants, thoracic spine implants, lumbar spine implants, glenohumoral joint, hip joints, wrists, plates for both cervical and lumbar spine.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
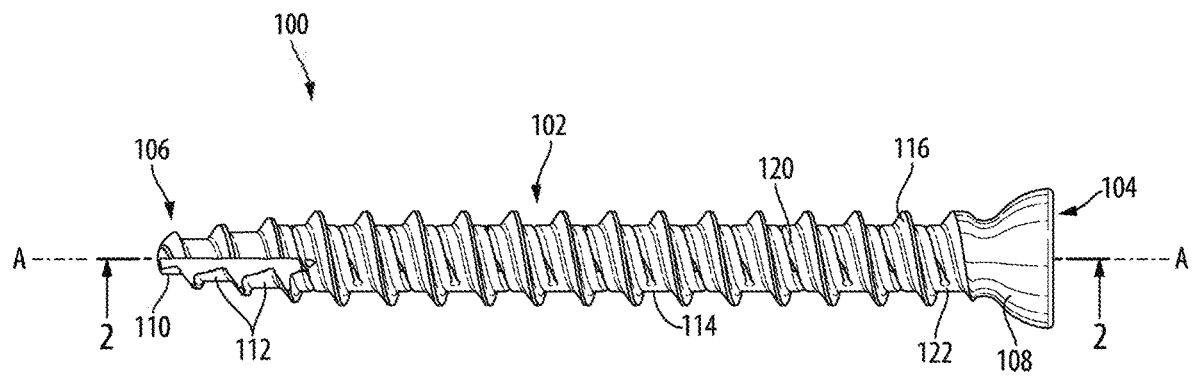
FIG. 1 is a side elevation view of an embodiment of a bendable fastener constructed in accordance with the present disclosure, showing the thread, the land, and the flexure openings.

Reference will now be made to the drawings wherein like reference numerals identify similar structural features or aspects of the subject disclosure. For purposes of explanation and illustration, and not limitation, a partial view of an embodiment of a bendable fastener in accordance with the disclosure is shown in FIG. 1 and is designated generally by reference character 100. Other embodiments of systems in accordance with the disclosure, or aspects thereof, are provided in FIGS. 2-12, as will be described. The systems and methods described herein can be used to provide flexure of fasteners such as orthopedic screws and nails with improved strength and flexibility relative to traditional configurations.

With reference to FIGS. 1-4, in accordance with at least one aspect of this disclosure, a flexible (e.g., bendable) fastener 100 can include a shaft 102 having a proximal end 104 and a distal end 106 spaced apart along a longitudinal axis A. In embodiments, a head 108 can be included at the proximal end 104 of the shaft 102 configured to engage a driver (not shown) for turning the fastener 100 about the longitudinal axis A. The distal end 106 of the shaft can define a narrowing tip 110 that tapers down along the longitudinal axis A in a distal direction. In certain embodiments, the narrowing tip 110 can include a self-tapping recess 112. In certain embodiments, the narrowing tip 100 can include a self-drilling feature.

A land surface 114 can be wound helically around the shaft 102. In embodiments, an external thread 116 can wind helically round the shaft 102. The land surface 114 can be wound helically around the shaft 102 axially offset from the external thread 116 so that the land surface 114 alternates with the external thread 116 in an axial direction along the shaft 102. The external thread 116 can extend in a radial direction beyond the land surface 114. In certain embodiments, the fastener 100 may not include any external thread 116 (e.g., such as for use as an intramedullary nail). In embodiments, the land surface 114 and/or the external thread can wind about the shaft 102 at constant intervals or variable intervals, or both. In certain embodiments, the external thread 116 can be or include cortical (e.g. threads having a finer pitch) and/or a cancellous (e.g., threads having a larger pitch) style threads.

Figure 2:
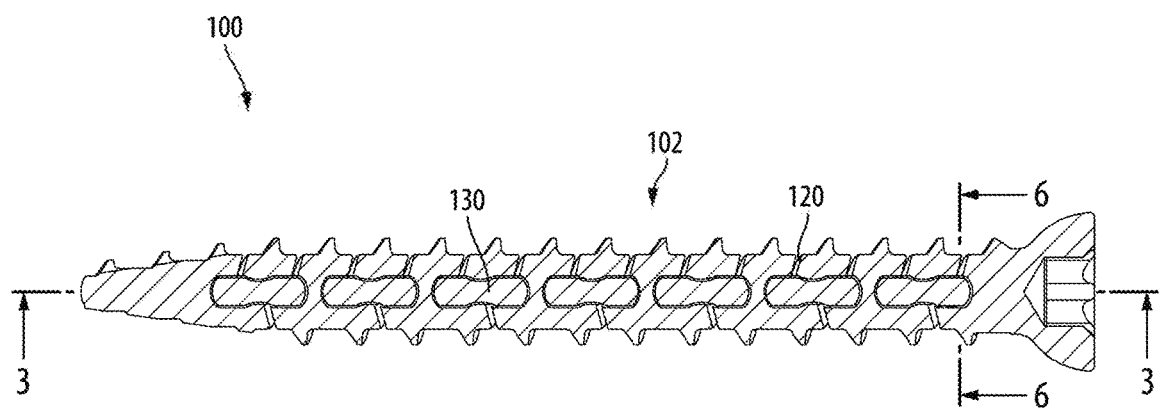
FIG. 2 is a cross-sectional plan view of the bendable fastener of FIG. 1, looking upward as oriented in FIG. 1, showing the torque drivers in the interior pockets.
Figure 3:
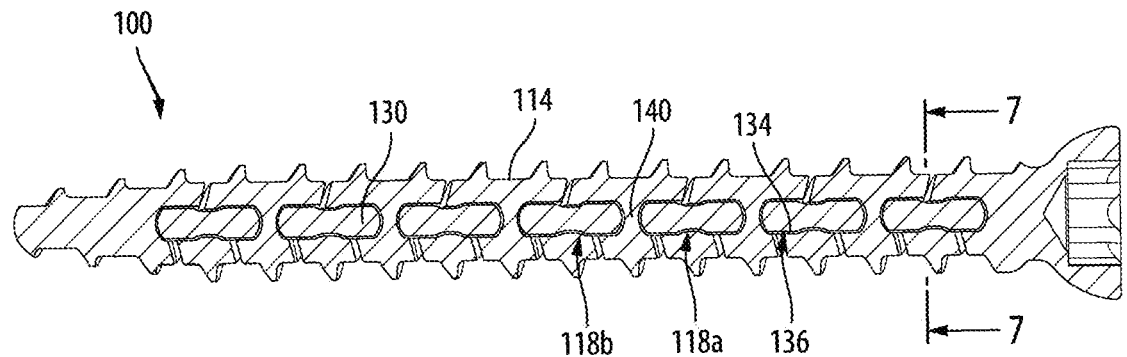
FIG. 3 is a cross-sectional side elevation view of the bendable fastener of FIG. 1, showing the torque faces of the torque drivers not visible in FIG. 2.
Figure 4:
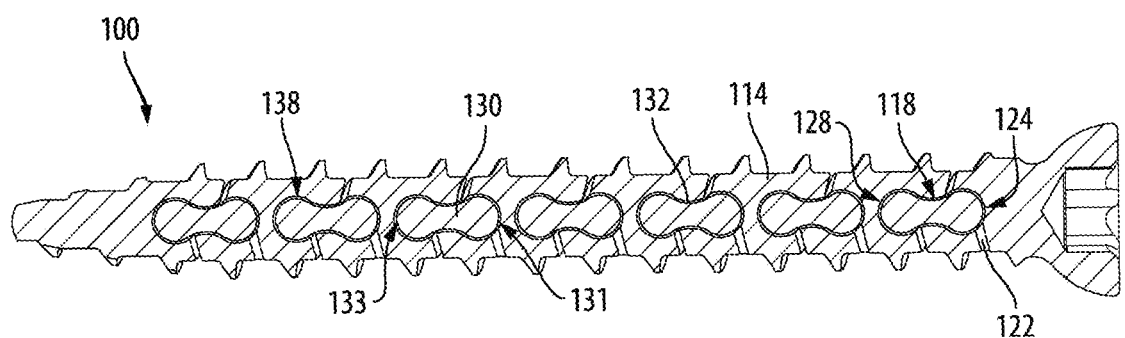
FIG. 4 is a cross-sectional oblique elevation view of the bendable fastener of FIG. 1, showing the diagonal-cross sections of the torque drivers relative to the views of FIGS. 2 and 3.

With reference to FIGS. 2-4 and 8-11, an interior pocket 118 can extend in an axial direction inside the shaft 102, radially inward from the land surface 114. A flexure 120 opening extends through the shaft 102 in the radial direction from the land surface 114 to an inward facing surface of the interior pocket 118. The flexure opening 120 can extend helically about the longitudinal axis A to provide for flexure of the shaft 102, of the land surface 114, and the external thread 116, and the flexure opening 120 can extend helically in parallel with the external thread 116. In embodiments, a proximal end 122 of the flexure opening 120 can be axially proximate a proximal end 124 of the interior pocket 118 with respect to the longitudinal axis A (e.g., as can be seen in FIG. 4).

Figure 9:
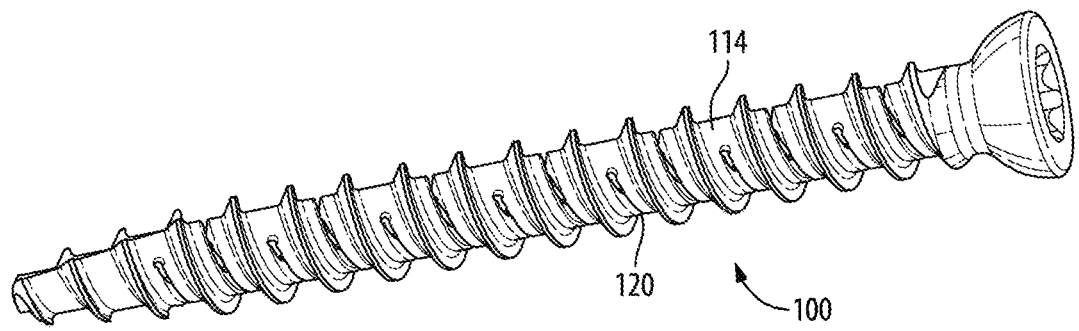
FIG. 9 is a perspective view of the bendable fastener of FIG. 1, showing the distal cul-de-sac shaped ends of the flexure openings, whereas the proximal cul-de-sac shaped ends are shown in FIG. 1.
Figure 11:
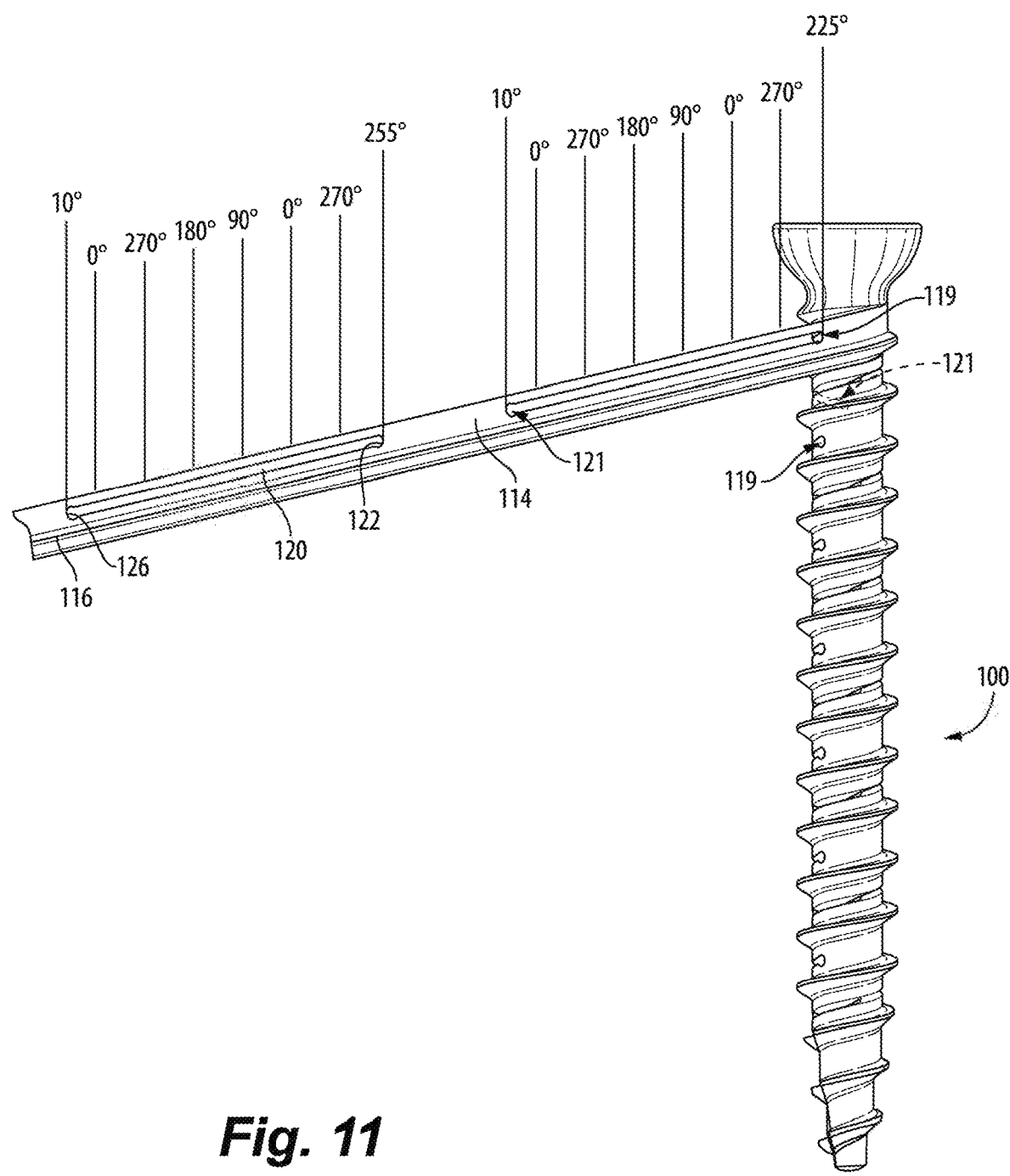
FIG. 11 is a schematic view of the bendable fastener of FIG. 1, showing a portion of thread, land, and flexure openings as though they are unwound from the helix, with angular locations as designated in FIG. 5 labeled.

The flexure opening 120 can wind around the interior pocket 118 to a distal end 126 of the flexure opening 120 that is proximal to a distal end 128 of the interior pocket 118. In FIGS. 1-4, the distal end 126 of the flexure opening 120 is on a backside of the fastener 100 and is out of view. FIG. 9 shows a rotated perspective view wherein the distal end 126 of the flexure opening 120 is visible, but wherein the proximal end 122 of the flexure opening 120 is not visible. The "unwound" schematic view shown in FIG. 11 shows both the proximal 122 and distal 126 ends of the flexure opening 120. In embodiments, the distal end 126 of the flexure opening 120 can define a distal stress-reducing cul-de-sac shape, and the proximal end 122 of the flexure opening 120 can define a proximal stress-reducing cul-de-sac shape (e.g., as best seen in FIG. 11).

Figure 5:
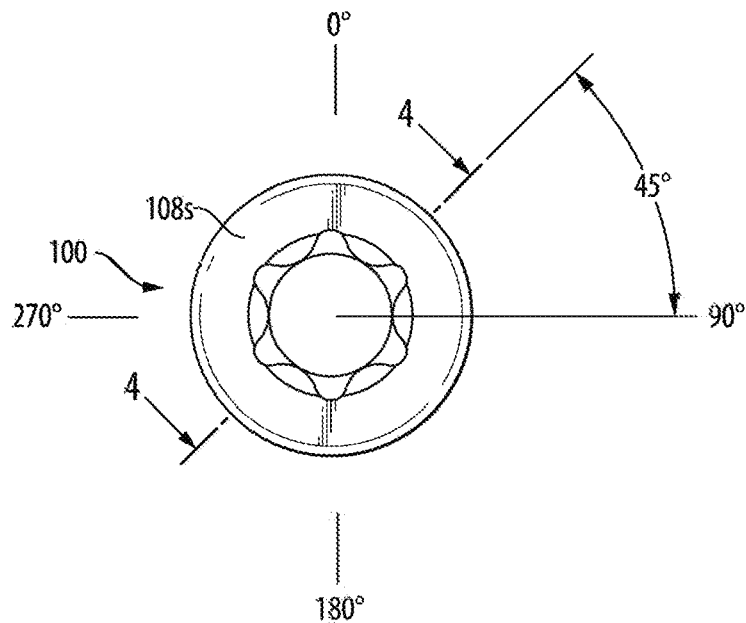
FIG. 5 is an end elevation view of the head of the bendable fastener of FIG. 1, showing the angle of cross-section for FIG. 4.

With further reference to FIG. 11, in certain embodiments, the flexure opening 120 can wrap beyond 360° around the interior pocket 118 circumferentially relative to the longitudinal axis A. For example, FIG. 11 shows a partially "unwound" fastener 100 where the proximal end 122 of the flexure opening 120 can begin at a first location 119 and the distal end 126 of the flexure opening 120 can terminate at a second location 121 on the fastener 100. In FIG. 5, a circumferential scale is defined looking down at the head 108 of the fastener as oriented in FIG. 5. This angular position scale is partially replicated on FIG. 1. In the view of FIG. 1, the circumferential position of 0° is the top of the fastener 100, 180° is the bottom, 90° is the side of the fastener facing into the page, and 270° is the side of the fastener facing out of the page. Transferring this scale to the view of FIG. 11, it can be seen that the first location 119 is at a position between 180° and 270°, but much closer to 270° than 180°. The first location 119 can be defined as 225° for example. The flexure opening 120 then extends around the shaft 102 (e.g., wrapping in a direction into the page), past 270° for a first time, past 0° for a first time, past 180°, past 90°, past 270° for a second time, past 0° for a second time, until termination at the second location 121 at some position between 0° and 90°, but much closer to 0° than 90°. The second location 121 can be defined as 10° on the circumferential scale. The circumferential scale is shown in a planar view on the unwound portion of FIG. 11.

With reference to FIGS. 1-7, 10, and 10A, a torque driver 130 is seated in the interior pocket 118. In certain embodiments, the flexure opening 120 can be too small to admit the torque driver 118 therethrough so the torque driver 130 is captured in the interior pocket 118. In embodiments, the torque driver 130 can be free floating within the interior pocket 118 (e.g., not integral with or affixed to) when the shaft 102 is in a relaxed state where no torque is applied to the shaft 102. In embodiments, the interior pocket can include a proximal portion 124 housing a proximal portion 131 of the torque driver 130 connected by a narrowing neck 129. The interior pocket 118 can also include a distal portion 128 housing a distal portion 133 of the torque driver 133. In embodiments, the interior pocket 118 can define a narrowing neck 132 connecting between the proximal and distal portions 124, 128 through which the narrowing neck 129 of the torque diver 130 passes.

The toque driver 130 can have a torque face 134 configured to abut a torque face 136 of the interior pocket 118 to develop toque along the shaft when a driving torque is applied to the proximal end 104 of the shaft 102. The torque face 134 of the torque driver 130 can be a first torque face 134a of the proximal portion 131 of the torque driver 130 and the proximal portion 131 of the torque driver 130 can include at least one additional torque face 134b, c, d. In embodiments, the distal portion 133 of the torque driver 130 can include a plurality of torque faces 134, e.g., at least 134e, f, g. Each of the torque faces 134 of the torque driver can face a corresponding torque face 136 of the interior pocket 118 for abutment and for engaging the corresponding torque face 136 when torque is applied to the head 108 to drive the torque from the proximal end 104 to the distal end 106 of the shaft 102.

Figure 6:
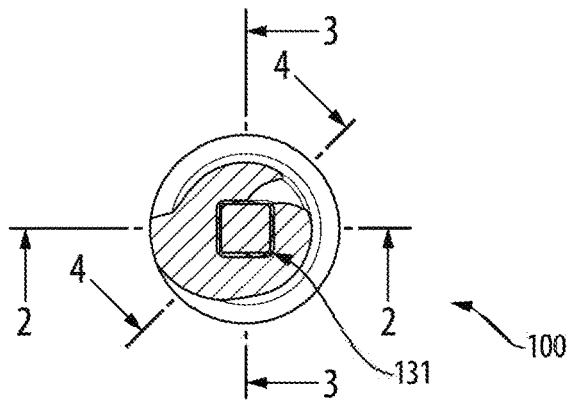
FIG. 6 is a cross-sectional end elevation view of the bendable fastener of FIG. 1, showing the axial cross-section of one of the torque drivers at the position indicated in FIG. 2.
Figure 7:
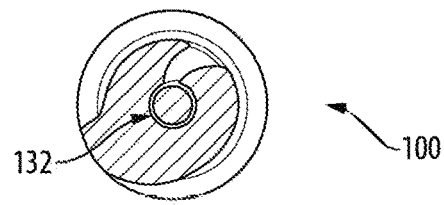
FIG. 7 is a cross-sectional end elevation view of the bendable fastener of FIG. 1, showing the axial cross-section through the narrowing neck of the toque driver.
Figure 8:
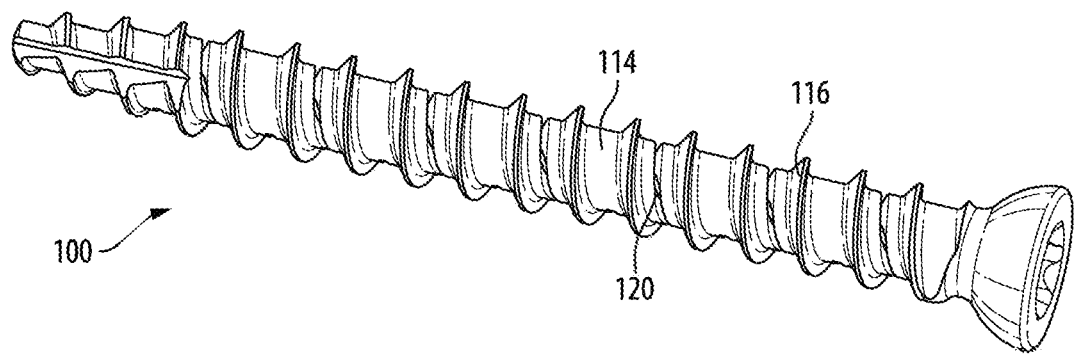
FIG. 8 is a perspective view of the bendable fastener of FIG. 1, showing portions of the land that do not have flexure openings.

In embodiments, a clearance gap 138 can be defined between the toque driver 130 and the interior pocket 118 so the toque driver 130 can move (e.g. by gravity as a user moves the fastener through a space such as an operating room) within the interior pocket 118 as long as the shaft 102 is in the relaxed state. The clearance gap 138, torque faces 134 of the torque driver 130, and the torque faces 136 of the interior pocket 118 can be configured so the clearance gap 138 is too small to allow the rotation of the torque driver 130 about the longitudinal axis A beyond a point where the torque faces 134, 136 of the interior pocket 118 and of the torque driver 130 come into abutment. The distal and proximal portions 131, 133 of the torque driver 130 can define a square axial cross-section with a diagonal too large to rotate within the interior pocket 118 beyond abutment of the torque faces 134, 136 (e.g., as shown in FIGS. 2, 3, and 6). In certain embodiments, abutment (e.g., as used herein) may not necessarily require full planar contact or engagement between faces. The narrowing neck 132 of the torque driver can define a circular axial cross-section (e.g., as shown in FIG. 7).

Figure 10:
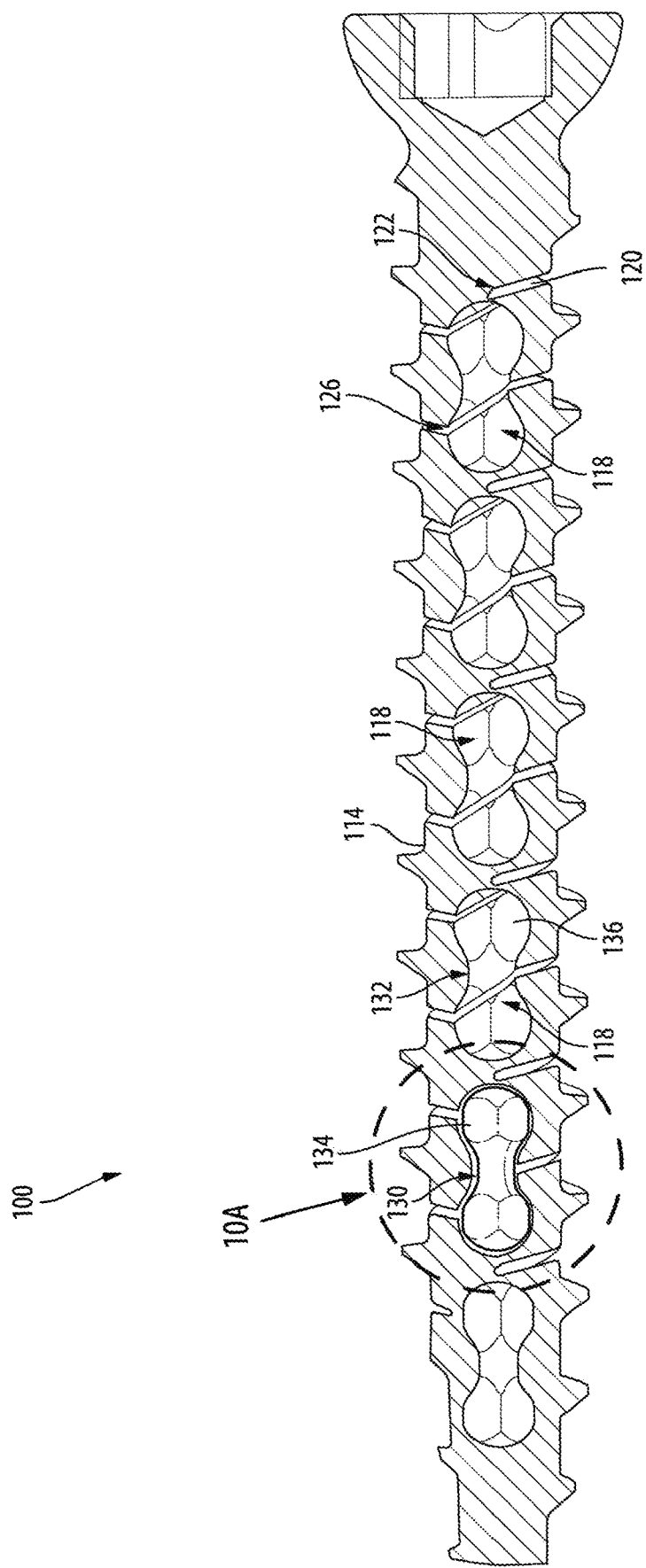
FIG. 10 is a side elevation view of the torque driver of FIG. 4, showing some of the torque faces.
Figure 10A:
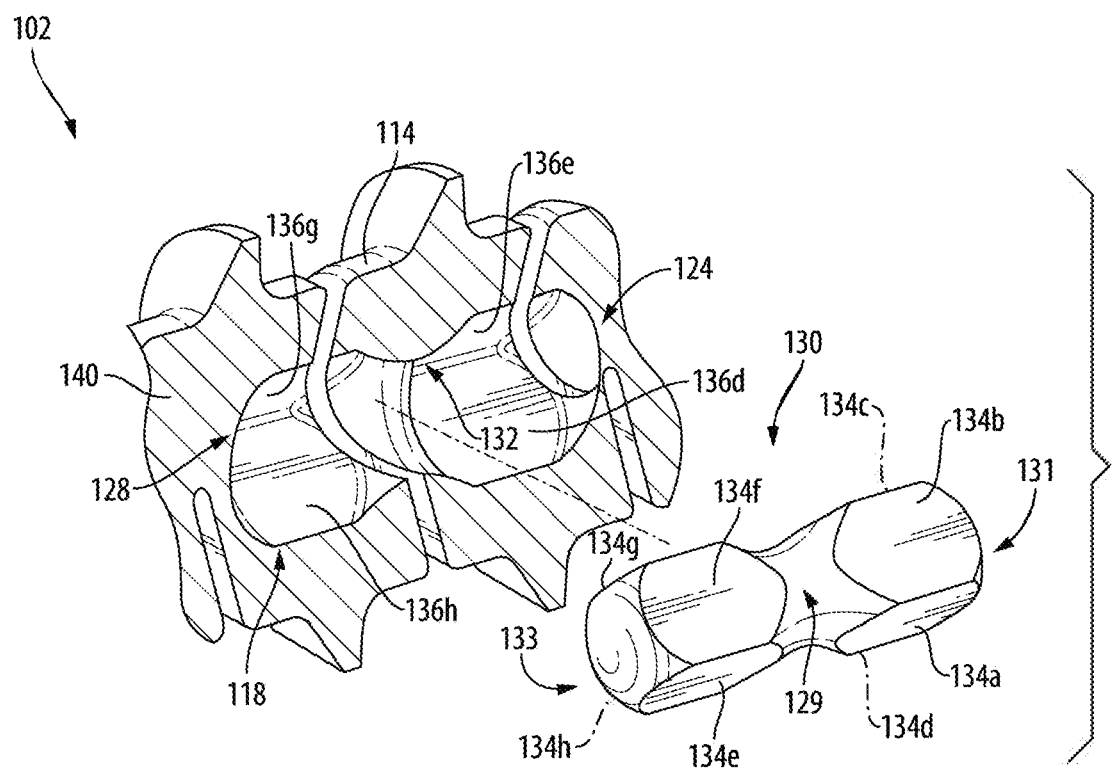
FIG. 10A is an enlarged exploded perspective view of a portion of FIG. 10, showing a torque driver exploded out of a respective interior pocket.

As can be seen most clearly in FIGS. 4 and 10, in embodiments, the proximal and distal portions 131, 133 of the torque driver 130 can have a cul-de-sac cross-sectional shapes in a plane of the diagonal. In certain embodiments, the proximal and distal portions 131, 133 of the torque driver 130 can be aligned along the same diagonal. In certain embodiments the proximal and distal portions 131, 133 of the torque driver 130 can be clocked about the longitudinal axis A relative to one another.

In embodiments, e.g., as shown, the interior pocket 118 can be a first interior pocket 118a and the fastener 100 can include at least one additional interior pocket 118b extending in an axial direction inside the shaft 102, radially inward from the land surface 114, and axially spaced apart from the first interior pocket 118 by a solid internal wall 140 of the shaft 102. In certain embodiments, the flexure opening 120 can overlap axially with the first interior pocket 118a but not with the second interior pocket 118b. Each interior pocket 118 can include a respective torque driver 130 as described above. The flexure opening 120 can be a first flexure opening in a plurality of flexure openings each opening into and overlapping axially with a respective one of the plurality of interior pockets 118. In certain embodiments, each of the flexure openings 120 can have a proximal end 122 and a distal end 126, where the proximal ends 122 of the flexure openings 120 can all terminate at a first circumferential position (e.g., a clock position) relative to the longitudinal axis A and the distal ends 126 of the flexure openings can all terminate at a second circumferential position relative to the longitudinal axis A. For example, as shown in FIGS. 1, and 11, the proximal ends 122 of the flexure openings 120 are shown at the first circumferential position, and FIG. 9 shows the distal ends 126 of the flexure openings 120 at the second circumferential locations.

Figure 12:
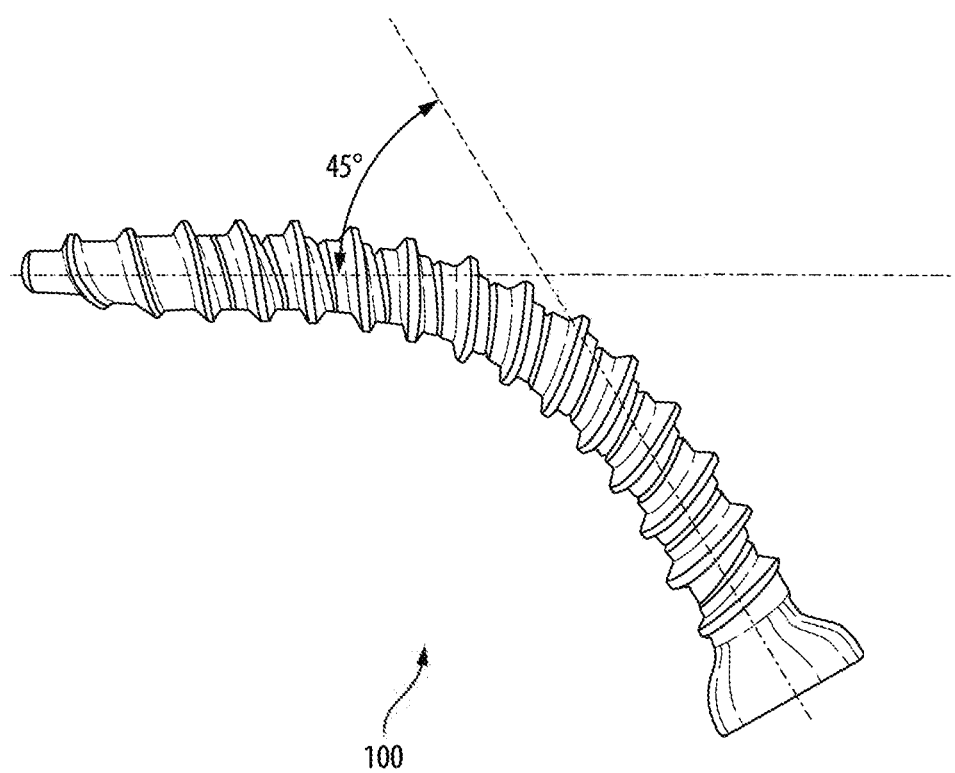
FIG. 12 is a perspective view of the bendable fastener of FIG. 1, showing the fastener bending.

In certain embodiments, the fastener 100 can be additively manufactured and the torque drivers 130 can be captured inside the interior pockets 118. In certain embodiments, the fastener 100 can be of titanium and can be additively manufactured from titanium. In certain embodiments, the fastener 100 can be of a biocompatible material or a combination of one or more biocompatible materials. In certain embodiments, the fastener 100 can be configured to bend up to and beyond 45° off of the longitudinal axis A (e.g., as shown in FIG. 12). In embodiments, the fastener 100 can be used for surgical or orthopedic applications, for example, vertebral spacers, acetabular cups, glenoid fossa prostheses, scaphoid prostheses, cervical spine implants, thoracic spine implants lumbar spine implants, glenohumoral joint, hip joints, wrists, or the like. U.S. Pat. No. 9,597,199 to Glazer, which is herein incorporated by reference in its entirety, describes embodiments of fasteners for various implants.

The methods and systems of the present disclosure, as described above and shown in the drawings, provide for flexure of fasteners such as orthopedic screws and nails with improved strength and flexibility relative to traditional configurations. While the apparatus and methods of the subject disclosure have been shown and described with reference to preferred embodiments, those skilled in the art will readily appreciate that changes and/or modifications may be made thereto without departing from the scope of the subject disclosure. For example, it is contemplated that the flexible shaft as described herein can be incorporated into tools other than fasteners, such as drills, awl drivers, or other shafted tools, and the flexible shaft need not include a head or pointed tip in such embodiments, but it may. Embodiments may include a flexible shaft alone or may be configured as a different type of driving member, such as a drill bit.

What is claimed is:

1. A flexible fastener comprising:
   a shaft having a proximal end and a distal end spaced apart along a longitudinal axis;
   a land surface winding helically around the shaft;
   an interior pocket extending in an axial direction inside the shaft, radially inward from the land surface;
   a flexure opening extending through the shaft in the radial direction from the land surface to an inward facing surface of the interior pocket, wherein the flexure opening extends helically about the longitudinal axis to provide for flexure of the shaft, of the land surface; and
   a torque driver seated in the interior pocket, the toque driver having a torque face configured to abut a torque face of the interior pocket to develop toque along the shaft when a driving torque is applied to the proximal end of the shaft.

2. The fastener as recited in claim 1, wherein the torque driver is free floating within the interior pocket, with the shaft in a relaxed state where no torque is applied to the shaft.

3. The fastener as recited in claim 1, wherein the torque driver includes a proximal portion and a distal portion with a narrowing neck connecting the distal portion to the proximal portion.

4. The fastener as recited in claim 3, wherein the torque face of the torque driver is a first torque face of the proximal portion of the torque driver, wherein the proximal portion of the torque driver includes at least one additional torque face, and wherein the distal portion of the torque driver includes a plurality of torque faces.

5. The fastener as recited in claim 4, wherein the interior pocket includes a proximal portion housing the proximal portion of the torque driver, wherein the interior pocket includes a distal portion housing the distal portion of the torque driver, and wherein the interior pocket defines a narrowing neck connecting between the proximal and distal portions of the interior pocket through which the narrowing neck of the torque driver passes.

6. The fastener as recited in claim 5, wherein each of the torque faces of the distal portion of the torque driver faces a corresponding torque face of the distal portion of the interior pocket for abutment, and wherein each of the torque faces of the proximal portion of the torque driver faces a corresponding torque face of the proximal portion of the interior pocket for abutment.

7. The fastener as recited in claim 6, wherein a clearance gap is defined between the toque driver and the interior pocket so the toque driver can move within the pocket as long as the shaft is in the relaxed state, but wherein the clearance gap and torque faces of the torque driver and of the interior pocket are configured so the clearance gap is too small to allow the rotation of the torque driver about the longitudinal axis beyond a point where the torque faces of the interior pocket and of the torque driver come into abutment.

8. The fastener as recited in claim 7, wherein the distal and proximal portions of the torque driver define a square axial cross-section with a diagonal too large to rotate within the interior pocket beyond abutment of the torque faces.

9. The fastener as recited in claim 8, wherein the proximal and distal portions of the torque driver have cul-de-sac cross-sectional shapes in a plane of the diagonal.

10. The fastener as recited in claim 9, wherein the narrowing neck of the torque driver defines a circular axial cross-section.

11. The fastener as recited in claim 1, wherein the flexure opening is too small to admit the torque driver therethrough so the torque driver is captured in the interior pocket.

12. The fastener as recited in claim 11, wherein a proximal end of the flexure opening is axially proximate a proximal end of the interior pocket with respect to the longitudinal axis, and wherein the flexure opening winds around the interior pocket to a distal end of the flexure opening that is proximal to a distal end of the interior pocket.

13. The fastener as recited in claim 12, wherein the flexure opening wraps beyond 360° around the interior pocket circumferentially relative to the longitudinal axis.

14. The fastener as recited in claim 13, wherein the distal end of the flexure opening defines a distal stress-reducing cul-de-sac shape, and wherein the proximal end of the flexure opening defines a proximal stress-reducing cul-de-sac shape.

15. The fastener as recited in claim 1, wherein the interior pocket is a first interior pocket and further comprising a second interior pocket extending in an axial direction inside the shaft, radially inward from the land surface, and axially spaced apart from the first interior pocket by a solid internal wall of the shaft, wherein the flexure opening overlaps axially with the first interior pocket but not with the second interior pocket.

16. The fastener as recited in claim 1, wherein the interior pocket is a first interior pocket in a plurality of interior pockets spaced apart axially along the longitudinal axis within the shaft, wherein the torque driver is a first torque driver in a plurality of torque drivers each seated in respective one of the plurality of interior pockets, and wherein the flexure opening is a first flexure opening in a plurality of flexure openings each opening into and overlapping axially with a respective one of the plurality of interior pockets.

17. The fastener as recited in claim 16, wherein each of the flexure openings has a proximal end and a distal end, wherein the proximal ends of the flexure openings all terminate at a first circumferential position relative to the longitudinal axis, and wherein the distal ends of the flexure openings all terminate at a second circumferential position relative to the longitudinal axis.

18. The fastener as recited in claim 1, further comprising an external thread winding helically round the shaft, wherein the land surface winds helically around the shaft axially offset from the external thread so that the land surface alternates with the external thread in an axial direction along the shaft, wherein the external thread extends in a radial direction beyond the land surface, and wherein the flexure opening extends helically in parallel with the external thread.

19. The fastener as recited in claim 1, further comprising a head at the proximal end of the shaft configured to engage a driver for turning the fastener about the longitudinal axis, wherein the distal end of the shaft defines a narrowing tip that tapers down along the longitudinal axis in a distal direction.

20. The fastener as recite in claim 19, wherein the narrowing tip includes a self-tapping or self-drilling feature.

* * * * *